(12) United States Patent
Stefko

(10) Patent No.: US 6,317,482 B1
(45) Date of Patent: Nov. 13, 2001

(54) RADIOLOGICAL IMAGE QUALITY INDICATOR

(75) Inventor: Eugene J. Stefko, Indian Head, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/107,315

(22) Filed: Jun. 30, 1998

(51) Int. Cl.[7] .................................................. G01D 18/00
(52) U.S. Cl. ................................ 378/56; 378/58; 378/207
(58) Field of Search ................................. 378/56, 58, 207

(56) References Cited

U.S. PATENT DOCUMENTS

| | | | |
|---|---|---|---|
| 5,276,726 | * | 1/1994 | Galkin ................................... 378/207 |
| 5,528,649 | * | 6/1996 | Heidsieck ............................. 378/207 |
| 5,771,272 | * | 6/1998 | Berger et al. ........................ 378/207 |
| 5,822,396 | * | 10/1998 | Navab et al. ......................... 378/207 |
| 5,841,835 | * | 11/1998 | Aufrichtig et al. .................. 378/207 |
| 5,844,965 | * | 12/1998 | Galkin ................................... 378/207 |
| 5,910,975 | * | 6/1999 | Floye et al. .......................... 378/207 |
| 6,041,094 | * | 3/2000 | Russell ................................... 378/37 |

OTHER PUBLICATIONS

Engineering specifications for GE Phantom 46–241852G1, Aug. 1985, 4 sheets.*

* cited by examiner

*Primary Examiner*—Drew Dunn
(74) *Attorney, Agent, or Firm*—Jacob Shuster

(57) ABSTRACT

An image quality indicator for determining the quality of an image is disclosed which includes a flat sheet of material of predetermined thickness having a series of elongated slots of various widths and a series of round holes formed therein, the elongated slots and round holes running through the entire thickness of the flat sheet. When energy from a source of radiation is directed through an object whose structural integrity is to be tested, viewing the image formed on an imaging device by a beam of energy following passage through the image quality indicator and the test object provides an indication of the contrast sensitivity and spatial resolution of the formed image.

4 Claims, 1 Drawing Sheet

RADIOLOGICAL IMAGE QUALITY INDICATOR

This invention is assigned to the United States Government as represented by the Secretary of the Navy.

BACKGROUND OF THE INVENTION

This invention relates to nondestructive testing and more particularly to that type of nondestructive testing in which it is desired to examine a test object or material to determine its structural integrity, such as for example, to determine the existence of cracks, voids, fissures, separations, foreign materials and inclusions as well as the dimensions of such imperfections. In such test systems, an energy source such as an x-ray generator is located at a predetermined distance from the object under test and the energy is directed through the test object to an imaging device, for example, a film sensitive to x-rays, to form an image of the object under test; in this example, a radiological image. It is desirable in such testing to have a means (called an image quality indicator (IQI)) to assess the quality of the (radiological) image formed. Radiological image quality comprises contrast sensitivity and spacial resolution. Contrast sensitivity is a measure of the minimum percentage change in an object which produces a perceptible density (brightness) change in the radiological image. Spacial resolution is a measure of the minimum size of an area of differing density (brightness) within an object which can be perceived on the radiological image.

In the past, radiological image quality was determined through the use of plack and wire penetrameters. Plack penetrameters measure contrast sensitivity and are fabricated as a flat sheet in different material or sheet thicknesses and contain a number of holes of various sizes through the thickness of the sheet. Wire penetrameters are fabricated by mounting lengths of material of various diameters on a flat sheet of material and are intended to measure spatial resolution. When used as radiological image quality indicators, the plack penetrameter and the wire penetrameter are deployed on the object to be tested and energy from a source (x-ray radiation) is directed through the penetrameters and the test object to an imaging device (x-ray film). Interpretation of the image formed on the imaging device provides an indication of the image quality. Additional information on radiological image quality indicating may be found in the 1997 Annual Book of ASTM Standards un Volume 03.03 Nondestructive Testing.

One problem with the prior art image quality indicators is that when the test object is relatively small, it is difficult to mount both a plack penetrameter and a wire penetrameter on the test object to obtain both contrast sensitivity and spatial resolution simultaneously. Further, since a wire penetrameter places additional material in the energy (x-ray) path, the quality is degraded, particularly when testing for voids, cracks, fissures and the like where it is the absence of material that is being tested for.

Accordingly, it is an object of this invention to provide an image quality indicator which determines contrast sensitivity and spatial resolution simultaneously.

It is a further object of this invention to provide an image quality indicator which provides a more accurate determination of image quality.

SUMMARY OF THE INVENTION

In accordance with the present invention, the image quality indicator is formed from a flat sheet of radiation opaque material of uniform thickness. The dimensions of the sheet thickness as well as width of slots and diameter of holes formed in the sheet, through which x-ray radiation passes into the test object, are selected to provide indications of image quality levels including contrast sensitivity and spatial resolution of the formed image.

DETAILED DESCRIPTION OF THE PREFERRED EMBODIMENTS

Figure 1:
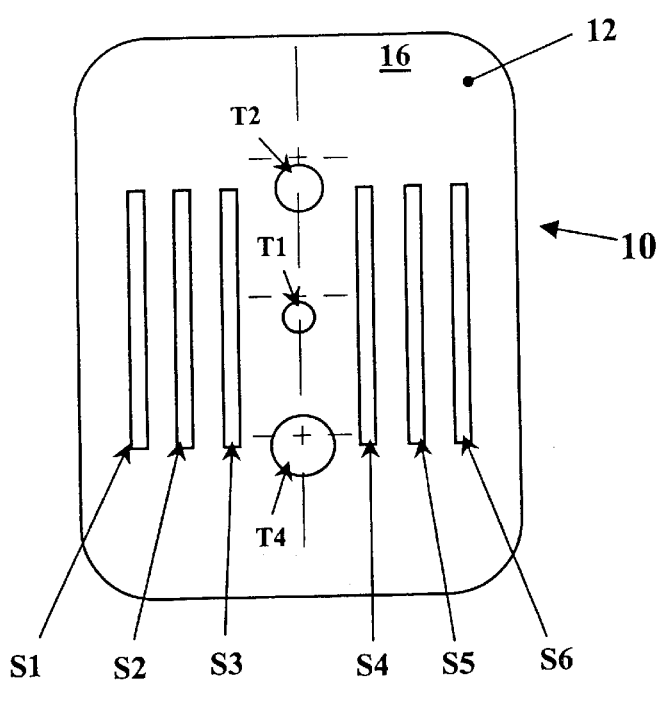
FIG. 1 is plan view of an image quality indicator according to this invention.
Figure 2:
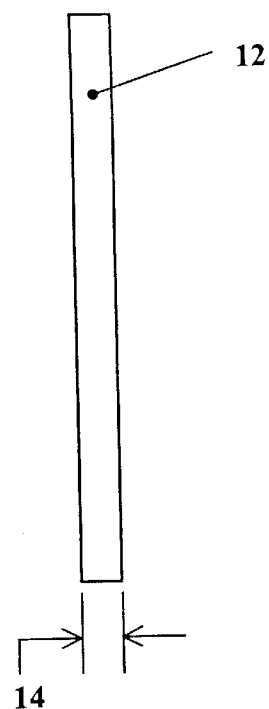
FIG. 2 is a side view of the image quality indicator of FIG. 1.

Referring now to the drawings there is shown a preferred embodiment of this invention. In FIGS. 1 and 2, a radiological image quality indicator according to this invention is shown generally at 10. The image quality indicator 10 is a flat sheet of material 12 which is the same as or radiologically similar to the material of the object under test. Indicator 10 may be encapsulated with a protective coating of material which is transparent to the energy (x-ray radiation) directed through it. In addition, the surface of the sheet 12 may have information such as sheet thickness and material type formed of a material opaque to the energy (x-ray) directed through it. The sheet 12 has a thickness 14 that is uniform throughout as shown in FIG. 2. Such thickness is selected based on the desired level of image quality. In this embodiment, following ASTM standards, the thickness 14 is selected to be 2% of the thickness of the object (not shown) to be tested. The object thickness used to determine the sheet thickness is a net thickness, that is, it does not include the thickness of any cavities which are in the test object by design. Image quality indicator 10 also includes six elongated slots S1, S2, S3, S4, S5 and S6 running through the thickness of the sheet 12 and range in width from 0.005 inches to 0.030 inches. The slot widths are selected based on sizes of the cracks, voids, fissures and the like which it is desired to test for. Image quality indicator 10 also includes openings or holes t1, t2 and t3 through the thickness of the sheet 12 having diameters which range from 0.035 to 0.140 inches. The level of image quality (sensitivity) is a function of image quality indicator thickness and hole diameter.

In operation, image quality indicator 10 is located as close as possible to the object under test to avoid image problems resulting from the divergence of beam of x-ray radiation to be directed through it. A beam of energy (x-ray radiation) is directed through the image quality indicator 10 and the object under test to a target to form an image on an imaging device such as an x-ray film luminescent tube or the like. Analysis of the image formed permits determination of the level of image quality including simultaneous determination of the contrast sensitivity and spatial resolution of the formed image. The slots S1 etc permit determination of the existence and size of fissures, cracks, voids and the like more easily because of the absence of material at those locations. In addition, other anomalies such as inclusions, foreign materials and the like are easily detected or simulated on the indicator. It will be understood that the image quality indicator can be formed of a variety of materials, in various thicknesses and with a range of hole and slot sizes depending on the object under test and the form of image forming energy transmitted through the image quality indicator and test object.

What is claimed is:

1. An image quality indicating device for determining the quality of an image of a test object formed by passing energy through the image quality device and the test object to an imaging target, comprising: a flat sheet of material of predetermined uniform thickness having a series of elongated slots of different selected widths and a series of round openings of different diameters running through the uniform thickness of the material, whereby examination and analysis of the image formed on the imaging target by the energy passing through said slots and the round openings provides an indication of quality level as a function of said uniform thickness of the flat sheet of the material and diameter of the round openings.

2. An image quality indicating device as set forth in claim 1 wherein the energy passing therethrough is x-ray radiation, the imaging target is x-ray film and the image of the test object is radiological.

3. An image quality indicating device as defined in claim 1, wherein said analysis of the image quality level includes simultaneous determination of contrast sensitivity and spatial resolution of the image formed by said energy on the imaging target.

4. In combination with a method of determining structural integrity of a test object by directing radiation therethrough from a source to a form an image on an imaging target; providing an indication of image quality level, comprising the steps of: positioning a sheet of material having a uniform thickness opaque to said radiation between the source and the test object; forming passages of slots of selected varying widths and holes in the sheet of material having uniform thickness extending the thickness thereof for conduction of the radiation to the imaging target; and selecting dimensions for the thickness of the sheet of the material and the passages to establish by analysis said indication of the image quality level simultaneously in terms of contrast sensitivity and spatial resolution as functions of the thickness of the sheet of material and diameter of the holes.

* * * * *